(12) United States Patent
Helmer

(10) Patent No.: US 12,128,220 B2
(45) Date of Patent: Oct. 29, 2024

(54) DATA COLLECTION DEVICE

(71) Applicant: Sanofi, Paris (FR)

(72) Inventor: Michael Helmer, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/309,542

(22) Filed: Apr. 28, 2023

(65) Prior Publication Data

US 2023/0256174 A1    Aug. 17, 2023

Related U.S. Application Data

(63) Continuation of application No. 16/652,449, filed as application No. PCT/EP2018/076731 on Oct. 2, 2018, now Pat. No. 11,672,913.

(60) Provisional application No. 62/569,357, filed on Oct. 6, 2017.

(30) Foreign Application Priority Data

Nov. 13, 2017 (EP) ..................... 17306568

(51) Int. Cl.
   *A61M 5/315*   (2006.01)
   *A61M 5/31*    (2006.01)
   *G16H 20/17*   (2018.01)
   *G16H 40/67*   (2018.01)

(52) U.S. Cl.
   CPC .......... *A61M 5/3155* (2013.01); *G16H 20/17* (2018.01); *G16H 40/67* (2018.01); *A61M 2005/3126* (2013.01); *A61M 2205/3306* (2013.01); *A61M 2205/3317* (2013.01); *A61M 2205/3584* (2013.01); *A61M 2205/50* (2013.01); *A61M 2205/587* (2013.01); *A61M 2205/6045* (2013.01)

(58) Field of Classification Search
   CPC ........ A61M 5/3155; A61M 2005/3126; A61M 2205/3306; A61M 2205/3317; A61M 2205/3584; A61M 2205/50; A61M 2205/587; A61M 2205/6045
   See application file for complete search history.

(56) References Cited

U.S. PATENT DOCUMENTS

| 6,666,849 B1 * | 12/2003 | Marshall ........... A61M 5/31553 |
| | | 604/207 |
| 9,604,004 B2 | 3/2017 | Jakobsen |
| 2011/0295215 A1 | 12/2011 | Nielsen et al. |
| 2012/0072236 A1 | 3/2012 | Atkin |

(Continued)

FOREIGN PATENT DOCUMENTS

| CN | 1179050 | 4/1998 |
| CN | 102105186 | 6/2011 |

(Continued)

OTHER PUBLICATIONS

International Preliminary Report on Patentability in Application No. PCT/EP2018/076731, dated Apr. 8, 2020, 7 pages.

(Continued)

*Primary Examiner* — Dung T Ulsh
(74) *Attorney, Agent, or Firm* — Bond, Schoeneck & King, PLLC

(57) ABSTRACT

A data collection device for attachment to an injection device and for collecting medicament dosage information therefrom.

20 Claims, 4 Drawing Sheets

(56) References Cited

U.S. PATENT DOCUMENTS

| | | | | |
|---|---|---|---|---|
| 2015/0018775 A1* | 1/2015 | Groeschke | ........ | A61M 5/31568 |
| | | | | 604/207 |
| 2016/0333579 A1 | 11/2016 | Stein | | |
| 2018/0200452 A1* | 7/2018 | Marcoz | .............. | G01R 33/0206 |
| 2019/0022330 A1* | 1/2019 | Schleicher | ........ | A61M 5/31546 |
| 2019/0298932 A1 | 10/2019 | Reisenhus | | |
| 2020/0282145 A1 | 9/2020 | Helmer | | |

FOREIGN PATENT DOCUMENTS

| | | |
|---|---|---|
| CN | 205670817 | 11/2016 |
| CN | 107061948 | 8/2017 |
| EP | 3058970 | 8/2016 |
| WO | WO 2010/065726 | 6/2010 |
| WO | WO 2016/131713 | 8/2016 |
| WO | WO 2016/198516 | 12/2016 |
| WO | WO 2017/013464 | 1/2017 |
| WO | WO 2017/148857 | 9/2017 |

OTHER PUBLICATIONS

International Search Report and Written Opinion in Application No. PCT/EP2018/076731, dated Nov. 27, 2018, 9 pages.

* cited by examiner

DATA COLLECTION DEVICE

CROSS-REFERENCE TO RELATED APPLICATIONS

The present application is a continuation of the U.S. patent application Ser. No. 16/652,449, filed Mar. 31, 2020, the national stage entry of International Patent Application No. PCT/EP2018/076731, filed on Oct. 2, 2018, and claims priority to Application No. EP 17306568.1, filed on Nov. 13, 2017, and Patent Application No. 62/569,357, filed on Oct. 6, 2017, the disclosures of which are incorporated herein by reference.

TECHNICAL FIELD

The present disclosure relates to a data collection device for attachment to an injection device and for collecting medicament dosage information therefrom.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dose setting dial and observing the actual dose from a dose window or display of the insulin pen. The dose is then injected by inserting the needle into a suited skin portion and pressing the dose setting dial or an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin dose.

SUMMARY

In one aspect, a data collection device for releasable attachment to a rotatable dose setting dial of a medicament administration device includes a cavity configured to receive the dose setting dial, a coupling member disposed within the cavity on an inner surface of the data collection device and configured to releasably couple the data collection device to the dose setting dial, and an orientation element disposed within the cavity on the inner surface of the data collection device and configured to engage with an indentation disposed on the dose setting dial.

In some embodiments, the data collection device includes a first end, a second end opposing the first end, and a wall extending between a portion of a periphery of the first end and a portion of a periphery of the second end. The first end, the second end and the wall together define the cavity. The second end includes a notch configured to receive a dial sleeve of the medicament delivery device, and the wall includes a slot configured to permit insertion of the dose setting dial of the medicament delivery device through the slot and into the cavity.

In some embodiments, the coupling member is disposed within the cavity on an inner surface of the first end.

In some embodiments, the orientation element is disposed on an inner surface of the wall of the data collection device.

In some embodiments, the coupling member is configured to couple the data collection device to the dose setting dial when the dose setting dial is received in the cavity of the data collection device.

In some embodiments, the coupling member includes a resiliently deformable member.

In some embodiments, the orientation element is a protrusion extending from the inner surface of the data collection device.

In some embodiments, rotation of the data collection device relative to the dose setting dial is prevented when the orientation element of the data collection device is engaged with the indentation on the dose setting dial.

In some embodiments, when attached to the dose setting dial of the medicament administration device, rotation of the data collection device causes rotation of the dose setting dial.

In some embodiments, the device has a generally cylindrical shape.

In some embodiments, the data collection device further includes a light source configured to illuminate a portion of a surface of a component of the medicament administration device including one or more relatively reflective regions formed on the surface of the component and an optical sensor configured to receive light reflected by at least the relatively reflective regions.

In some embodiments, the data collection device further includes a window configured to allow light emitted by the light source to pass through it.

In some embodiments, the data collection device has a longitudinal axis and is configured to be mounted onto the dose setting dial by (i) orienting the data collection device such that the longitudinal axis is parallel to an axis of rotation of the dose setting dial and such that the orientation element is aligned with the indentation on the dose setting dial and (ii) moving the data collection device in a perpendicular direction with respect to the axis of rotation of the dose setting dial.

In another aspect, a dose setting dial is configured to be releasably coupled to one of the data collection devices described above.

In some embodiments, the dose setting dial includes a channel configured to releasably couple with the coupling member of the data collection device and an indentation configured to engage with the orientation element of the data collection device.

In some embodiments, the dose setting dial further includes a window.

In a further aspect, a system includes a medicament administration device including a housing, a rotatable dose setting dial, a dial sleeve at least partially located within the housing and including one or more relatively reflective regions formed on the surface of the dial sleeve, and one of the data collection devices described above. The dial sleeve and dose setting dial are rotationally coupled during dose setting and dose resetting of the device and rotationally decoupled during dose dispensing of the device.

In an additional aspect, a system includes one of the dose setting dials described above and one of the data collection devices described above.

BRIEF DESCRIPTION OF THE FIGURES

FIG. 3b shows a perspective view of the dose setting dial of FIG. 3a.

DETAILED DESCRIPTION

In the following disclosure, embodiments will be described with reference to an insulin injection device. The present disclosure is however not limited to such application and may equally well be deployed with injection devices that eject other medicaments.

Figure 1:
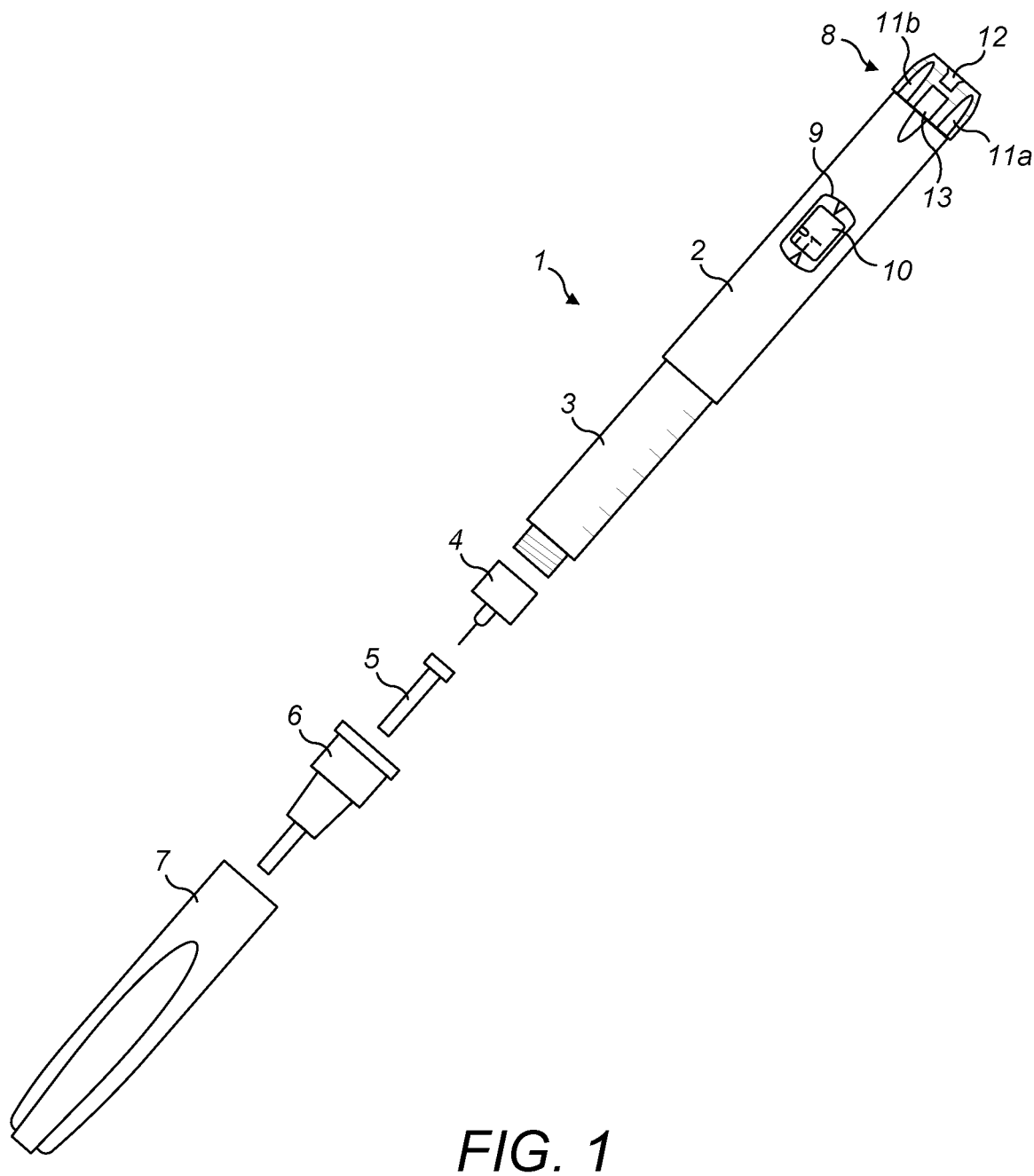
FIG. 1 shows an exploded view of an injection device for use with a data collection device.

FIG. 1 is an exploded view of a medicament administration device. In this example, the medicament administration device is an injection device 1, such as Sanofi's AllStar® insulin injection pen, however the present invention is also compatible with other types and makes of injection pens as described below.

The injection device 1 of FIG. 1 is a pre-filled injection pen that comprises a housing 2 and contains an insulin container 3, to which a needle 4 can be affixed. The injection device 1 may be disposable or re-usable. The needle is protected by an inner needle cap 5 and either an outer needle cap 6 or an alternative cap 7. An insulin dose to be ejected from injection device 1 can be programmed, or 'dialled in' by turning a dose setting dial 8 and a currently programmed dose is then displayed via dosage window 9, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 9 in FIG. 1.

The medicament delivery device 1 has distal and proximal ends. The term "distal" refers to a location that is relatively close to the site of injection, and the term "proximal" refers to a location that is relatively further away from the injection site. In the present embodiment, the needle 4 is situated towards the distal end of the device 1, whilst the dose setting dial 8 is situated towards the proximal end of the device 1. The device 1 has a longitudinal axis which extends between the proximal and distal ends of the device 1.

The dosage window 9 may be in the form of an aperture in the housing 2, which permits a user to view a limited portion of a number sleeve 10 that is configured to move when the dose setting dial 8 is turned, to provide a visual indication of a currently programmed dose. The number sleeve 10 may be a component which rotates when a dose is being dispensed from the injection device 1.

In this example, the dose setting dial 8 includes one or more formations 11a, 11b that facilitate programming because they improve the grip a user feels when grasping the dose setting dial 12. In another example (not shown) the dose setting dial does not include formations. Attaching a data collection device does not require the dose setting dial having formations.

The dose setting dial 8 comprises an indent or groove 12 which is configured to engage with a protruding orientation element positioned on a data collection device. When the groove 12 is engaged with the orientation element of the data collection device, the data collection device is in a pre-defined position. The orientation element helps to align the data collection device in a pre-defined position by aligning the groove 12 of the dose setting dial with the orientation element of the data collection device.

The stability of the connection between the data collection device and the dose setting dial may be increased. For example, having a tight fit and/or using rubber-like material at the contact surface between the data collection device and the injection device would provide an attachment that, on the one hand, facilitates a stable connection in the sense that the two devices remain attached to each other and, on the other hand, allows the two devices to be separated when desired. The rubber-like material would ensure a proper fit even on a smooth surface, e.g., a dose setting dial having a smooth surface such that that rotation of the data collection device causes rotation of the dose setting dial and vice versa.

The dose setting dial 8 further comprises a window 13 which is configured to allow the passage of light through the dose setting dial 8 and onto an internal component of the medicament delivery device 1. The window 13 is further configured to allow light reflected by an internal component of the medicament delivery device 1 to pass through and the window 13 and out of the device.

The dose setting dial 8 is configured to be rotated to set a dose. This causes the dose setting dial 8 to move proximally away from the housing 2. When a dose is dispensed from the injection device 1, the dose setting dial 8 moves back (distally) towards the housing 2 but does not rotate. Rotation of the dose setting dial 8 also causes the dial sleeve 10 to move proximally out of the housing 2. When a dose is dispensed from the injection device 1, the dial sleeve 10 rotates and moves back (distally) into the housing 2, but the dose setting dial 8 does not rotate.

The injection device 1 may be configured so that turning the dose setting dial 8 causes a mechanical click sound to provide acoustical feedback to a user. The number sleeve 10 mechanically interacts with a piston in insulin container 3. When needle 4 is stuck into a skin portion of a patient, a user depresses the entire dose setting dial 8, which moves longitudinally relative to the housing 2, in order to cause the medicament to be dispensed. During this dispensing operation, the insulin dose displayed in display window 9 will be ejected from injection device 1. When the needle 4 of injection device 1 remains for a certain time in the skin portion after the dose setting dial 8 has been depressed, a high percentage of the dose is actually injected into the patient's body. Ejection of the insulin dose may also cause a mechanical click sound, which is however different from the sounds produced when using dose setting dial 8.

In the various embodiments, during delivery of the insulin dose, the dose setting dial 8 is returned to its initial position in an axial movement, that is to say without rotation, while the number sleeve 10 is rotated to return to its initial position, e.g. to display a dose of zero units.

Injection device 1 may be used for several injection processes until either the insulin container 3 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 3 and needle 4, for instance by selecting two units of insulin and pressing depressing the dose setting dial 8 while holding injection device 1 with the needle 4 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

Figure 2:
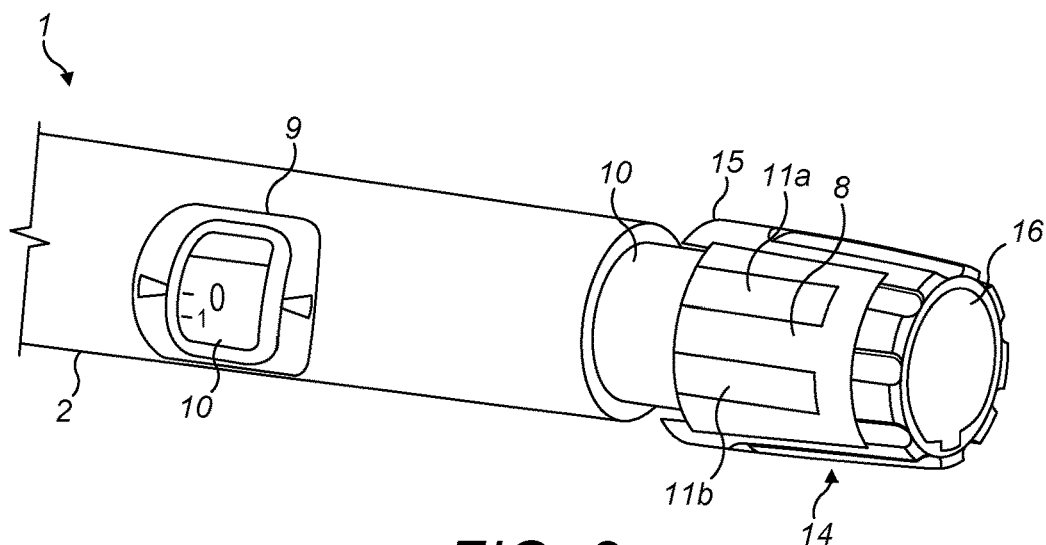
FIG. 2 depicts a data collection device, attached to the injection device of FIG. 1.

FIG. 2 is a perspective view of one end of the injection device 1 when a data collection device 14 according to an example embodiment is attached. The data collection device 14 includes a housing 15 with an end plate 16 forming a user interaction surface. The housing 15 may support an optical user feedback such as one or more LEDs (not shown). In some optional embodiments, the data collection device 14 comprises a display (not shown)

The data collection device 14 is compatible with a number of existing injection devices 1 which have an integrated dial. The data collection device 14 is compatible with injection devices where the dose setting dial does not rotate during dose administration, but where an internal component close to the dose setting dial does rotate during dose administration. The data collection device 14 allows the rotation of this internal component to be detected and measured.

Figure 3A:
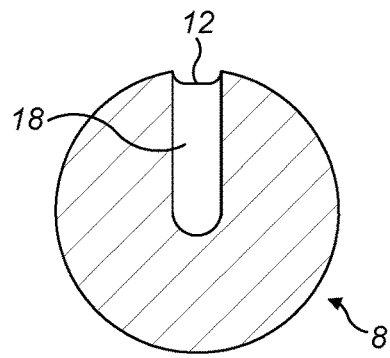
FIG. 3a shows a cross-sectional view of a dose setting dial of the injection device.
Figure 3B:
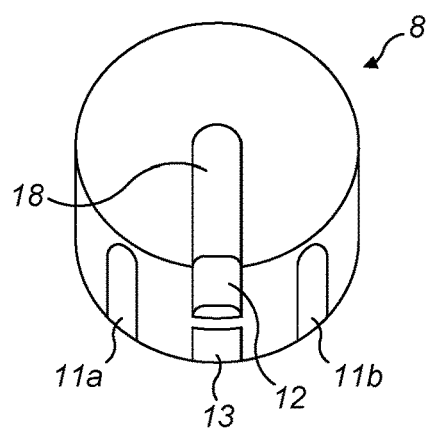

FIG. 3a is a top-down view of the dose setting dial 8 whilst FIG. 3b is a perspective view of the dose setting dial 8. The dose setting dial 8 is has a generally circular cross section and comprises groove 12 and a channel 18. As previously explained, groove 12 is configured to engage with an orientation element of a data collection device. The groove may be a depression or a indentation which extends partially into the body of the dose setting dial 8.

Channel 18 is configured to engage with a coupling member of the data collection device. The channel 18 is shaped such that it can receive a protrusion that is disposed on the data collection device. The shape of the channel 18 and the shape of the protrusion of the data collection device may complement each other.

Figure 4:
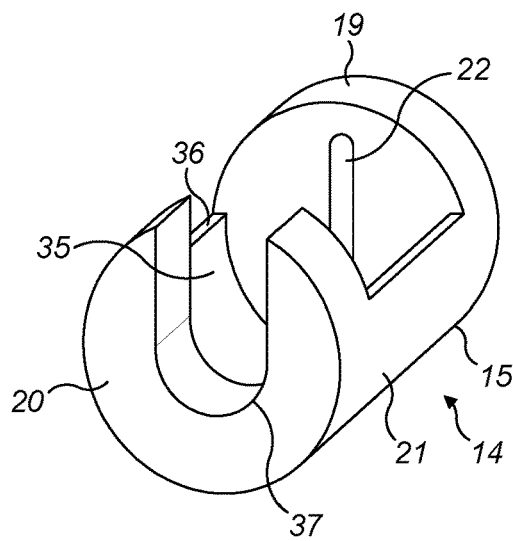
FIG. 4 depicts a cross-sectional view of the data collection device.

FIG. 4 is a perspective view of the data collection device 14 according to some embodiments. The housing 15 comprises a first end 19, a second end 20 which is opposite the first end 19 and a wall 21 which extends from at least a portion of the periphery of the first end 19 to at least a portion of the periphery of the second end 20. The first end 19, second end 20 and wall 21 together define a cavity 35 which is configured to receive the dose setting dial 8 of the medicament delivery device 1. Other components, such as an electronics assembly, may be contained within the housing.

The first end 19 may be a plate, such as a disc. Further components of the data collection device 14 may be contained within the housing 15 or be disposed on a surface of the housing 15. For example, a coupling member 22 may be disposed on the inner surface of the first end 19. Alternatively, the coupling member may be disposed on an inner surface of the wall 21 or the second end 20. Other components, such as an electronics assembly, may be contained within the body of the first end.

The second end 20 comprises a notch 37. The notch 37 may be configured to receive the dial sleeve 10 of the medicament delivery device 1.

The wall 21 comprises a slot 36 which is configured to permit insertion of the dose setting dial 8 into the cavity 35. The slot 36 has dimensions sufficient to allow for the dose setting dial to be inserted into the cavity 35. Alternatively, the slot 36 may deform to allow for the dose setting dial 8 to be inserted into the cavity 35. For example, the wall may be at least partially made from a deformable or a resiliently deformable material. Other components, such as an electronics assembly, may be contained within the body of wall 21.

The volume of the cavity 35 may be similar to, or substantially the same as, the volume of the dose setting dial 8. This will help the dose setting dial 8 to form a tight fit within the cavity 35 of the housing.

The coupling member 22 is configured to engage with channel 18 of the dose setting dial 8 when the data collection device 1 is mounted on the dose setting dial 8. The coupling member 22 may be a component that is attached to the housing 15, such as a resiliently deformable member (e.g. a spring or a spring-loaded clip). Alternatively, the coupling member 22 may be a component that is an integral part of the housing 15, such as a protrusion. In such embodiments, the protrusion may be made from a resiliently deformable material.

Figure 5:
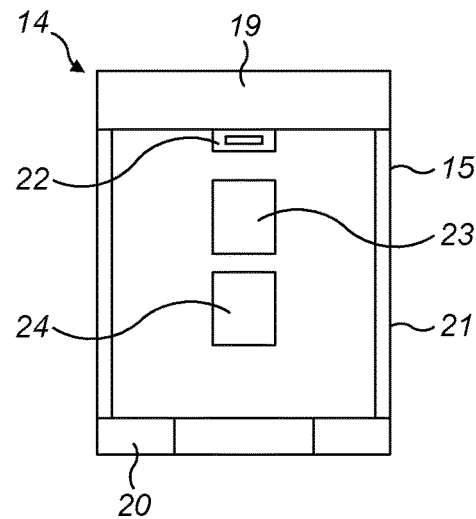
FIG. 5 shows a cross-sectional view of the data collection device.

FIG. 5 is a cross-sectional view of the data collection device 14 according to some embodiments.

The housing 15 may further comprises an orientation element 23 which is configured to engage with groove 12 located on the dose setting dial 8. The orientation element 23 may be a protrusion that projects from the inner surface of the wall 21. When the data collection device 14 is mounted on the dose setting dial 8, the orientation element 23 engages with the groove 12 of the dose setting dial 8. When the orientation element 23 is engaged with the groove 12 of the dose setting dial 8, the data collection device 14 is prevented from rotating relative to the dose setting dial 8, i.e. the dose data collection device 14 and dose setting dial 8 are rotatably locked.

The housing 15 may further comprise a sensor window 24 which is configured to allow light to pass into the data collection device from a light source located within the data collection device 14. The sensor window 24 may also be configured to allow light to pass through the sensor window 24 into the housing 15 and be received by an optical sensor located within the data collection device 14. In the illustrated embodiment, the sensor window 24 is located on an internal surface of the wall 21 and covers the light source 29 and optical sensor 30. In alternative embodiments, the sensor window 24 may be located on other internal surfaces of the data collection device, such as on an internal surface of the first end 19 or on an internal surface of the second end 20.

Figure 6:
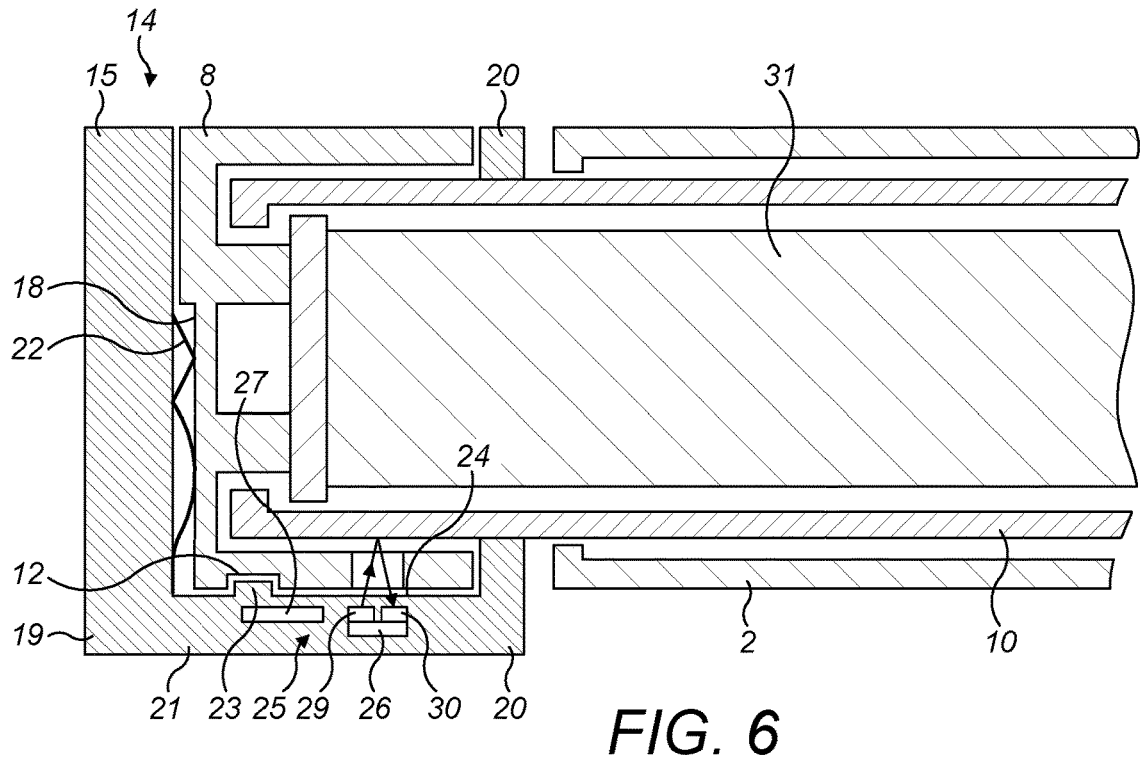
FIG. 6 shows a cross-sectional view of the data collection device, attached to the injection device of FIG. 1.

FIG. 6 is a cross-sectional view of the data collection device 14 according to some embodiments, when attached to the medicament delivery device 1.

When attached to the medicament delivery device 1, the dose setting dial at least partially fills the cavity 35 formed by the first end 19, the second end 20 and the wall 21 of the data collection device 14.

The data collection device 14 is configured so as to detect and measure the rotation of the dial sleeve 10 when attached to the injection device 1.

The dial sleeve 10 rotates during dose dispense. The data collection device 14 is configured so as to detect and measure the rotation of the dial sleeve 10 when attached to the injection device 1. The injection device 1 shown in FIG. 6 may also have other components which rotate when a dose is dispensed, such as a drive sleeve 31.

The data collection device 14 includes a housing 15 and an electronics assembly 25 disposed inside the housing 15. The coupling member 22 of the data collection device 1 is engaged with the channel 18 of the dose setting dial 8, whilst the orientation element 23 of the data collection device 14 is engaged with the groove 12 located on the dose setting dial 8.

The engagement of the coupling member 22 in the channel 18 helps to prevent the data collection device 14 from being removed from the dose setting dial 8 and it also provides a rotational lock.

When the dose setting dial 12 rotates during programming of the dosage, the data collection device 14 also rotates. The engagement of the orientation element 23 in the groove 12 helps to prevent the data collection device 14 from rotating independently of the dose setting dial 8.

Additionally, resilient padding, such as a foam rubber pad (not shown), may be provided between the inner surface of the data collection device 14 and the outer surface of the dose setting dial 8 to allow for tolerances in the dimensions of the dose setting dial 8 and the data collection device 14.

The electronics assembly 25 comprises a PCB 26 and a battery 27, for example in the form of a coin cell. The PCB 26 may support a number of components including a processor arrangement 28, a light source 29 and an optical sensor 30. In these embodiments, the light source 29 is an infrared light source and the optical sensor 30 is an infrared optical sensor. As shown in FIG. 6, in some embodiments, the light source 29 and optical sensor 30 are supported on the side of the PCB which abuts the dose setting dial 8.

The light source 29 transmits light through the sensor window 24 of the data collection device 14. The dose setting dial has a window 13 which is transparent or substantially transparent to light. Thus, the light emitted by the light source 29 passes through the dose setting dial 8 and illuminates the internal components. In particular the number sleeve 10 is a hollow cylinder which extends to the proximal end of the housing 2 and is releasably fixed to the dose setting dial 8. The cylindrical surface of the number sleeve 10 therefore sits underneath the dose delivery button 8 and is illuminated by the infrared light. The dial sleeve 10 is provided with a pattern of relatively reflective and non-reflective regions on the cylindrical surface. For example, equally spaced and equally sized reflective and non-reflective sections may be arranged alternately.

During a dose dispensing operation, the light source 29 illuminates the part of the number sleeve 10 including the pattern of relatively reflective and non-reflecting regions; and the optical sensor 30 receives the light reflected by at least the relatively reflective regions. The output of the optical sensor 30 is relayed to the processor 28 which calculates an amount of rotation of the number sleeve 10 during the dose dispensing operation. From the amount of rotation, the delivered dose can be calculated. This may be done by the data collection device 14 or by another computing device. In general, any component which is located close to the dose setting dial and which rotates when a dose is dispensed from the injection device 1 may be used as the internal component having the pattern of relatively reflective and non-reflective regions formed on a surface thereof.

The relatively reflective and non-reflective regions are disposed on an outer surface of the number sleeve 10, around the circumference. Such an arrangement may allow the reflective and non-reflective regions to be larger or spaced further apart as more space is available on this surface of the number sleeve 10.

This embodiment may allow the optical path to be minimized and to remain unchanged when the dose setting dial 8 is moved longitudinally relative to the dial sleeve 10 during dose dispensing. This adds to increased dose detection reliability. This embodiment also has a simple mechanical design and construction.

Instead of having a light source and optical sensor, the electronics assembly may comprise a non-contact magnetic sensor, for example a Hall Effect sensor. In this embodiment, the rotatable component 10 comprises a series of magnetic regions and non-magnetic regions, instead of relatively reflective and non-reflective regions, spaced alternately around the circumference of the rotatable component 10. The magnetic regions may be permanent magnets, such as regions containing magnetic particles or a magnetic ink. As the magnetic and non-magnetic regions rotate past the magnetic sensor during dose dispense, the magnetic sensor detects a periodic change in the strength and optionally direction of the magnetic field. This information can then be used to determine the amount (angle) of rotating of the rotatable component 10. The dose setting dial 8 is transmissive or partially transmissive to the magnetic field generated by the magnetic regions, allowing the magnetic sensor to detect rotation of the rotatable component 10 remotely and without the need for a cut-out or window in the dose setting dial 8.

When the data collection device 14 and injection device 1 are secured together, the electronics assembly 25 is configured to abut the dose setting dial 8. The data collection device 14 effectively replaces the dose setting dial, as the user interacts directly with the data collection device 14 in the same way as they would with the dose setting dial to set and deliver a dose of medicament.

The electronics assembly 25 comprises numerous components including a PCB 26, the light source 29, the optical sensor 30, a processor arrangement and a battery 27. In some embodiments, the light source 29 is an infrared light source and the optical sensor 30 is an infrared optical sensor. The window 13 of the dose setting dial is transparent or substantially transparent to infrared radiation. Thus the light emitted by the light source 29 passes through the window 13 of the dose setting dial 8 and illuminates the internal components. In particular the number sleeve 10 is a hollow cylinder which extends to the proximal end of the housing 2 and moves longitudinally with the dose setting dial 8 when a dose is set. The number sleeve 10 may be releasably fixed to the dose setting dial 8 such that the annular end surface of the dial sleeve 10 is sits underneath the dose delivery button 8 and is illuminated by the infrared light of the light source 29. The number sleeve 10 is provided with a pattern of relatively reflective and non-reflective regions on the cylindrical end surface. For example, equally spaced and equally sized reflective and non-reflective sections may be arranged alternately. Alternatively, the drive sleeve 31 or another internal component may be provided with the pattern of relatively reflective and non-reflective regions.

During a dose dispensing operation, the light source 29 illuminates a portion of the number sleeve 10 including a portion of the pattern of relatively reflective and non-reflecting regions; and the optical sensor 30 receives the light reflected by at least the relatively reflective regions as they pass underneath. The output of the optical sensor 30 is relayed to a processor (not shown) which calculates an amount of rotation of the number sleeve 10 during the dose dispensing operation. From the amount of rotation, the delivered dose can be calculated. This may be done by the data collection device or by another computing device.

In general it is necessary to know the type of the injection device 1 to which the data collection device 14 is attached in order to determine a dose of medicament which has been dispensed. Therefore, in some embodiments, the data collection device 14 measures only the amount of rotation of the internal component in degrees. This information is saved in a memory of the data collection device 14 and may be communicated by the data collection device 14 to an external computing device where it is combined with information about the type of injection device 1 in order to record the delivered medicament dose.

The fixed construction and design of the embodiment of the data collection device 14 in FIG. 6 has the advantage of a simple mechanical construction (e.g., by minimizing relative movements) which provides an accurately defined positioning of optical sensor 30 relative to the injection device housing and the internal component including the pattern of relatively reflective and non-reflecting regions (e.g., dose dial 8) according to this embodiment.

The medicament delivery device 1 comprises a longitudinal axis which extends between the proximal and distal ends of the medicament delivery device 1. The dose setting dial 8 is positioned towards the proximal end of the medicament delivery device 1 and the number sleeve 10 extends distally from the underside of the dose setting dial 8. The axis of rotation of the dose setting dial 8 and the number sleeve 10 corresponds to the longitudinal axis of the medicament delivery device 1.

To mount the data collection device 14 on the medicament delivery device 1 the orientation element 23 and the groove 12 on the dose setting dial 8 are aligned. In this position, the slot 36 of the wall 21 and the notch 37 of the second end 20 are positioned so that they face the medicament delivery device 1. The data collection device 14 is then moved towards the medicament delivery device 1 in a direction that is perpendicular to the longitudinal axis of the medicament delivery device 1. As the data collection device advances towards the medicament delivery device 1, the dial sleeve 10 is received in the notch 37 of the second end, whilst the dose setting dial 8 is received in the cavity 35 of the data collection device 1. As the dose setting dial is received into the cavity 35, the coupling member 22 of the data collection device 1 engages with the channel 18 of the dose setting dial 8, thereby coupling the data collection device 14 to the dose setting dial 8.

When the dose setting dial 8 is fully received in the cavity 35 of the data collection device 14, the orientation element 23 is in engagement with the indentation 12 of the dose setting dial 8. The orientation element 23 prevents the data collection device 14 from being incorrectly mounted on the dose setting dial 8 because in order to fully mount the data collection device 14 on the dose setting dial 8, the orientation element 23 must be received into the groove 12.

Attempting to mount the data collection device 14 onto the dose setting dial 8 in an incorrect orientation will be prevented by the orientation element 23. Thus, the data collection device 14 mounts onto the dose setting dial 8 in a pre-defined position.

Mounting the dose setting dial 8 in a predefined position on the dose setting dial 8 ensure that sensor window 24 of the data collection device 14 is in alignment with the window 13 of the dose setting dial 8. In this orientation, the light source 29 can illuminate the pattern of relatively reflective and non-reflective regions disposed on the internal component (e.g. number sleeve 10) of the medicament delivery device 1. The orientation element therefore aids alignment of the data collection device 14.

The data collection device 14 of the present disclosure attaches directly to the dose setting dial of the medicament administration device. Previous data collection devices have attached to the main housing of the medicament administration device. This can impede the use of the medicament administration device by a user. Many such devices attach over a dose indication window in the housing of the medicament administration device. This obscures the dose indication window, making the user wholly reliant on the data collection device to indicate the dialled dose, which may reduce user confidence in the medicament administration device. Some other such devices require an additional cut out or aperture in the housing of the medicament administration device in order to view or connect with an internal moveable component. Cutting out a part in the housing of the medicament administration device makes the ingress of dust and dirt inside the delivery mechanism more likely. It may also present problems relating to the sterility of the medicament administration device.

The data collection device of the present disclosure is able to monitor the amount of medicament dispensed from the medicament administration device remotely, without contacting or being secured to the main housing of the medicament administration device. The data collection device is configured to attach to and to effectively replace the part of the medicament administration device with which the user would normally interact. When a user wishes to dial a dose, they grasp and rotate the housing 15 of the data collection device 14 which in turn rotates the dose setting dial 8. The user can continue to observe the mechanical dose indication window 9 of the medicament administration device. When the user wishes to inject a dose, they exert a force on the proximal end of the data collection device. This in turn communicates a force to the dose setting dial. The user would notice no material difference in the way in which they operate the medicament administration device as a result of the addition of the data collection device according to the present invention.

The data collection device of the present disclosure may use infrared light as an illumination source. This allows the external components of the medicament administration device to be made out of a plastic or other material which is opaque to optical wavelengths, but transparent or partially transparent to Infrared wavelengths. No additional cut out, aperture or the like are required, although only the appropriate areas of the medicament administration device may be made of the IR transmissive material, effectively forming an Infrared 'window'.

The relatively reflective and non-reflective regions of the pattern may be printed, deposited, etched or otherwise created directly onto the number sleeve 10 or other suitable internal component during that component's manufacture. In some examples, the internal component is located in close proximity to the dose setting dial. The medicament administration device may then be assembled in the same way as before, using the same assembly method and tools. Therefore, only very minimal modification of the medicament administration device design and creation is required in order to implement the invention.

As discussed above in relation to FIG. 6, the light source 29 and optical sensor 30 in FIG. 6 may instead be replaced with a magnetic sensor. The relatively reflective and non-reflective regions of the pattern on the rotatable component 10 may be replaced by alternating magnetic regions and non-magnetic regions such that when the rotatable component 10 is rotated during a dose dispensing operation, there is a periodic change in the magnetic field detected by the magnetic sensor.

Figure 7:
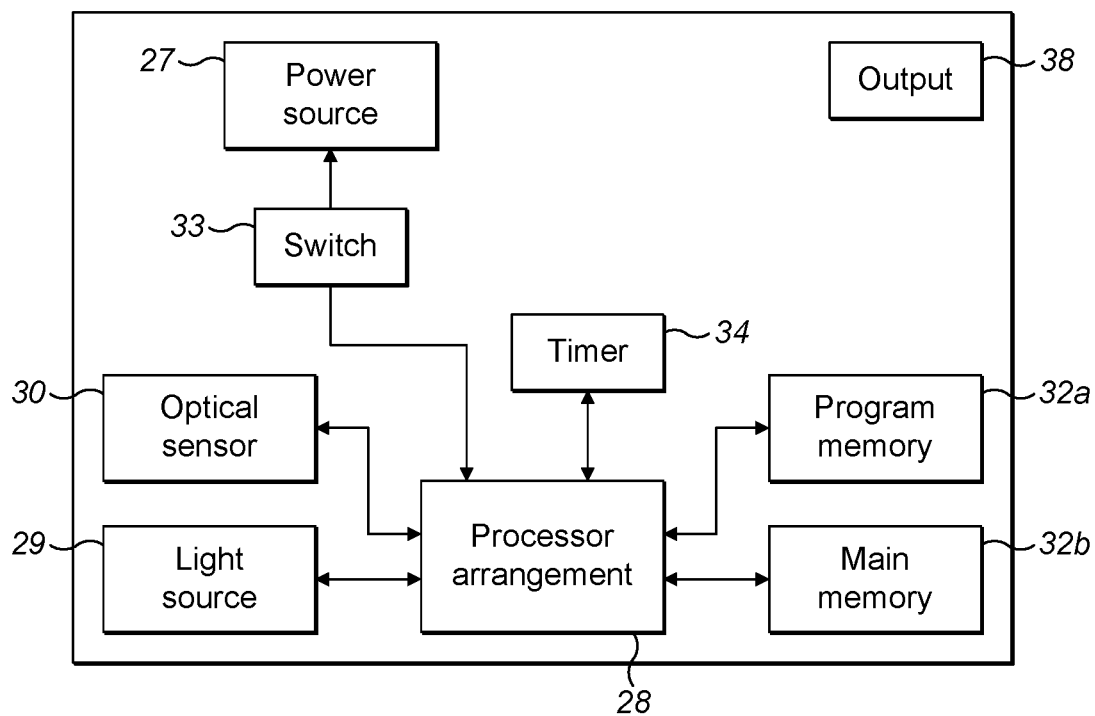
FIG. 7 is a block diagram of the data collection device.

FIG. 7 is a block diagram of the data collection device 14. The data collection device 14 includes a processor arrangement 28 including one or more processors, such as a microprocessor, a Digital Signal Processor (DSP), Application Specific Integrated Circuit (ASIC), Field Programmable Gate Array (FPGA) or the like, together with memory units 32a, 32b, including program memory 32a and main memory 32b, which can store software for execution by the processor arrangement 28. The data collection device includes the infrared light source 29 and the infrared optical sensor 30. The processor arrangement 28 controls operation of the light source 29 and the optical sensor 30 and receives signals from the optical sensor 30.

The data collection device 14 has a power source 27 which may be a battery, for example a coin cell. The data collection device 14 may optionally include a switch 33 configured to be triggered when or shortly before a dose is dispensed. To this end, the switch 33 may include a pressure or touch sensitive area in the end plate 16 of the data collection device 14, for example a piezoelectric switch. The switch 33 may control application of power from the power source 27 to the processor arrangement 28 and other components of the data collection device 14.

The switch may be a "wake-up" switch which, when operated, activates the data collection device 14. The wake-up switch may be implemented optically as an "optical wake-up sensor". In particular, the underlying rotatable component 10 may be white (or black). When the rotatable component 10 is rotated, the relatively reflective and non-reflective regions of the rotatable component 10 move in front of the optical wake-up sensor and the change in reflectance and/or colour can be detected, providing the wake-up signal for the other electronics. This change in reflectance or colour can also be used to determine the start and end times of an injection process. In this case a switch as described before may function to wake-up the electronics, including the light source and optical sensor and an optical switch may use the change in reflectance or colour to determine start and end times of an injection process. This could be helpful in determining if an injection process has occurred or if a priming process has occurred. Further, the colour/reflectance switch could be used to determine how long the button has been pressed and use this to see if a dwell time has been respected by the user.

A timer 34 is also included. The processor arrangement 28 may use the timer 34 to monitor a length of time that has elapsed since an injection was completed, determined using the switch 33. Also optionally, the processor arrangement 28 may compare the elapsed time with a predetermined threshold, to determine whether a user may be attempting to administer another injection too soon after a previous injection and, if so, generate an alert such as an audible signal and/or generate an optical signal such as blinking one or more LEDs. The data collection device 14 may comprise a number of LEDs or other light sources for providing optical feedback to a user. For example, the LEDs may use different colours and/or lighting patterns such as blinking with constant or changing periodicity. On the other hand, if the elapsed time is very short, it may indicate that the user is administering a medicament amount as a "split dose", and the processor arrangement 28 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 28 stores information indicating that the dosage was delivered as a "split dose". Another optional purpose for monitoring the elapsed time by the processor arrangement 28 is to determine when the elapsed time has passed a predetermined threshold, suggesting that the user might have forgotten to administer another injection and, if so, generate an alert.

The processor is further configured to store data relating to date and/or time information, data relating to information from the optical sensor 30, or combinations thereof. In particular, the memory is configured to store a combination of date and/or time information and internal component rotation information retrieved from the optical sensor 30 output data. In this way the memory is able to store a log that provides a history of information on number sleeve 10 (or other internal component) rotation. Data can for example be stored in the main memory 32a. Alternatively, data may be stored is a separate data storage section (not shown) of the memory.

Since the number sleeve or other internal component rotates as medicament is expelled from the injection device 1, the angle of rotation measured by the optical sensor 30 is proportional to the amount of medicament expelled. It is not necessary to determine a zero level or an absolute amount of medicament contained in the injection device 1. In this way the sensor arrangement is less complex than compared to a sensor arrangement that is configured for absolute position detection. Moreover, since it is not necessary to monitor the numbers or tick marks on the number sleeve 10 displayed through the dosage window 9, the data collection device 14 may be designed so that it does not obscure the dosage window 9.

Figure 8:
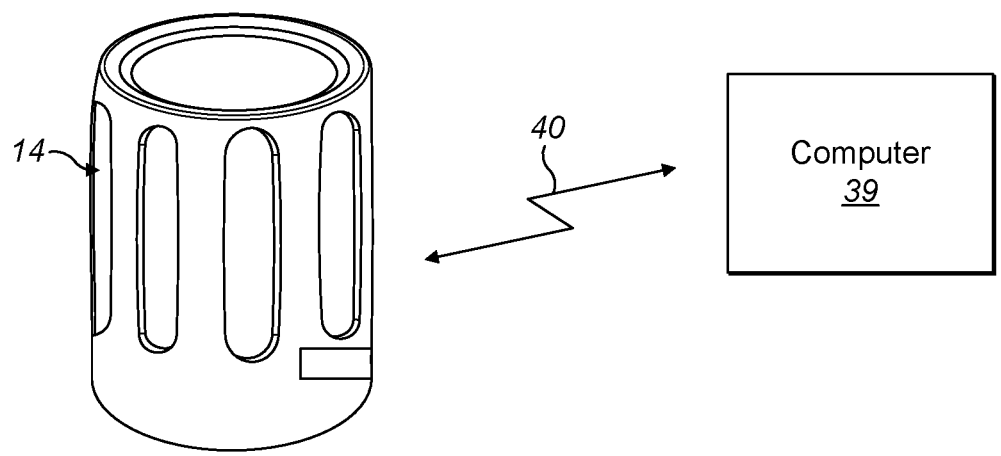
FIG. 8 shows a system in which the data collection device is connected to another device, such as a personal computer.

An output 38 is provided, which may be a wireless communications interface for communicating with another device via a wireless network such as wi-fi, Bluetooth®, or NFC, or an interface for a wired communications link, such as a socket for receiving a Universal Series Bus (USB), mini-USB or micro-USB connector. FIG. 8 depicts an example of a system in which the data collection device 14 is connected to another device, such as a personal computer 39, via a wireless connection 40 for data transfer. Alternatively or in addition, the data collection device 14 may be connected to another device via a wired connection. For example, the processor arrangement 28 may store determined number sleeve 10 rotation angles and time stamps (including date and/or time) for the injections as they are administered by the user and subsequently, transfer that stored data to the computer 39. The computer 39 may be configured to calculate an administered dose based on further information entered by the user or a medical professional regarding the type of injection device and the type of medicament.

The computer 39 maintains a treatment log and/or forwards treatment history information to a remote location, for instance, for review by a medical professional.

According to some embodiments, the data collection device 14 may be configured to store data such as number sleeve 10 rotation angles and time stamps of up to 35 injection events. According to a once-daily injection therapy this would be sufficient to store a treatment history of about one month. Data storage is organized in a first-in first-out manner ensuring that most recent injection events are always present in the memory of the data collection device 14. Once transferred to a computer 39 the injection event history in the data collection device 14 will be deleted. Alternatively, the data remains in the data collection device 14 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the output 58 may be configured to transmit information using a wireless communications link and/or the processor arrangement 28 may be configured to transmit such information to the computer 39 periodically.

The specific embodiments described in detail above are intended merely as examples of how the present invention may be implemented. Many variations in the configuration of the data collection device 14 and/or the injection device 1 may be conceived.

In particular, while the embodiments above have been described in relation to collecting data from an insulin injector pen, it is noted that embodiments of the disclosure may be used for other purposes, such as monitoring of injections of other medicaments. Although the data collection device has been described primarily as comprising a single infrared light source 29, the data collection device may comprise a plurality of light sources 29. The plurality of light sources 29 may be supported at different positions on the electronics assembly 25 and may be angled and or focused so as to illuminate a particular part of the internal component 10 from a particular angle when the data collection device is attached to the dose setting dial.

The data collection device 14 may optionally include a display (not shown), which could for example occupy the end plate 16 of the data collection device 14. Various information can be displayed, such as the length of time that has elapsed since an injection was completed, and warning messages where a user is attempting to administer another injection too soon after a previous injection.

The invention claimed is:

1. A data collection device for releasable attachment to a rotatable dose setting dial of a medicament administration device, the data collection device comprising a housing, the housing comprising:
   an electronics assembly;
   a first end;
   a second end opposing the first end;
   a cavity configured to receive the dose setting dial; and
   a wall extending between a portion of a periphery of the first end and a portion of a periphery of the second end, wherein the first end, the second end and the wall together define the cavity and wherein the wall comprises a slot located between the first end and the second end and configured to permit insertion of the rotatable dose setting dial of the medicament administration device through the slot and into the cavity, wherein the data collection device is configured such that, when the data collection device is attached to the rotatable dose setting dial, rotation of the housing of the data collection device causes rotation of the dose setting dial relative to a housing of the medicament administration device.

2. The data collection device of claim 1, wherein the data collection device comprises an orientation element disposed within the cavity on an inner surface of the wall of the data collection device and wherein the orientation element is configured to prevent relative rotation of the data collection device and the dose setting dial when the data collection device is attached to the dose setting dial.

3. The data collection device of claim 2, wherein the orientation element is a protrusion extending from the inner surface of the data collection device.

4. The data collection device of claim 1, wherein the data collection device has a longitudinal axis and is configured to be mounted onto the rotatable dose setting dial by:
   orienting the data collection device such that the longitudinal axis is parallel to an axis of rotation of the rotatable dose setting dial; and
   moving the data collection device in a perpendicular direction with respect to the axis of rotation of the dose setting dial.

5. The data collection device of claim 4, wherein an orientation element is aligned with an indentation on the rotatable dose setting dial when:
   the data collection device is oriented such that the longitudinal axis is parallel to an axis of rotation of the rotatable dose setting dial; and
   the data collection device is moved in a perpendicular direction with respect to the axis of rotation of the dose setting dial and mounted onto the dose setting dial.

6. The data collection device of claim 1, wherein the data collection device comprises a coupling member disposed within the cavity on an inner surface of the first end and wherein the coupling member is configured to engage with a channel of the dose setting dial.

7. The data collection device of claim 6, wherein the coupling member is configured to couple the data collection device to the rotatable dose setting dial when the rotatable dose setting dial is received in the cavity of the data collection device.

8. The data collection device of claim 1, wherein when the data collection device is attached to the dose setting dial, the first end of the data collection device is situated at a proximal end of the dose setting dial.

9. The data collection device of claim 1, wherein when the data collection device is attached to the dose setting dial, a portion of the dose setting dial is visible externally of the data collection device when the data collection device is attached to the dose setting dial.

10. The data collection device of claim 1, wherein the data collection device has a generally cylindrical shape.

11. The data collection device of claim 1, wherein the data collection device further comprises:
   a light source configured to illuminate a portion of a surface of a component of the medicament administration device including one or more relatively reflective regions formed on the surface of the component.

12. The data collection device of claim 11, wherein the data collection device comprises an optical sensor configured to receive light reflected by at least the relatively reflective regions.

13. The data collection device of claim 11, wherein the data collection device further comprises a window configured to allow light emitted by the light source to pass through the window.

14. The data collection device of claim 1, wherein the data collection device is configured to detect and measure rotation of a dial sleeve of the medicament administration device.

15. The data collection device of claim 1, wherein the data collection device comprises a non-contact magnetic sensor configured to detect magnetic regions on a rotatable component of the medicament administration device.

16. A system comprising:
a medicament administration device comprising a rotatable dose setting dial;
and a data collection device for releasable attachment to the rotatable dose setting dial of the medicament administration device, the data collection device comprising a housing, the housing comprising:
an electronics assembly;
a first end;
a second end opposing the first end;
a cavity configured to receive the dose setting dial; and
a wall extending between a portion of a periphery of the first end and a portion of a periphery of the second end, wherein the first end, the second end and the wall together define the cavity and wherein the wall comprises a slot located between the first end and the second end and configured to permit insertion of the rotatable dose setting dial of the medicament administration device through the slot and into the cavity, wherein the data collection device is configured such that, when the data collection device is attached to the rotatable dose setting dial, rotation of the housing of the data collection device causes rotation of the dose setting dial relative to a housing of the medicament administration device.

17. A system as claimed in claim 16, wherein the data collection device is attached to the rotatable dose setting dial of the medicament administration device.

18. A system as claimed in claim 16, wherein the data collection device is configured to be detached from the dose setting dial by moving the data collection device in a perpendicular direction with respect to an axis of rotation of the dose setting dial and relative to the dose setting dial.

19. A system as claimed in claim 16, wherein when the dose setting dial is received in the cavity of the data collection device, an orientation element of the data collection device is engaged with an indentation of the dose setting dial and a coupling member of the data collection device is engaged with a channel of the dose setting dial.

20. A system as claimed in claim 16, wherein the data collection device comprises an orientation element disposed within the cavity on an inner surface of the wall of the data collection device and wherein the orientation element is configured to prevent relative rotation of the data collection device and the dose setting dial when the data collection device is attached to the dose setting dial.

* * * * *